(12) United States Patent
Moussy et al.

(10) Patent No.: US 7,678,805 B2
(45) Date of Patent: *Mar. 16, 2010

(54) USE OF TYROSINE KINASE INHIBITORS FOR TREATING INFLAMMATORY BOWEL DISEASES (IBD)

(75) Inventors: Alain Moussy, Paris (FR); Jean-Pierre Kinet, Lexington, MA (US)

(73) Assignee: AB Science, Paris (FR)

( * ) Notice: Subject to any disclaimer, the term of this patent is extended or adjusted under 35 U.S.C. 154(b) by 126 days.

This patent is subject to a terminal disclaimer.

(21) Appl. No.: 10/482,033

(22) PCT Filed: Jun. 28, 2002

(86) PCT No.: PCT/IB02/03317

§ 371 (c)(1),
(2), (4) Date: Jul. 7, 2004

(87) PCT Pub. No.: WO03/004007

PCT Pub. Date: Jan. 16, 2003

(65) Prior Publication Data

US 2004/0266801 A1   Dec. 30, 2004

Related U.S. Application Data

(60) Provisional application No. 60/301,405, filed on Jun. 29, 2001.

(51) Int. Cl.
*A61K 31/505* (2006.01)
(52) U.S. Cl. ....................... 514/275; 514/269
(58) Field of Classification Search ................ 514/275, 514/269
See application file for complete search history.

(56) References Cited

U.S. PATENT DOCUMENTS

| | | | |
|---|---|---|---|
| 3,467,666 A | 9/1969 | Dexter et al. | |
| 3,558,653 A | 1/1971 | Coyne et al. | |
| 3,725,403 A | 4/1973 | Krapcho | |
| 4,587,342 A | 5/1986 | Daluge et al. | |
| 5,521,184 A | 5/1996 | Zimmerman | |
| 5,639,757 A | 6/1997 | Dow et al. | |
| 5,792,783 A | 8/1998 | Tang et al. | |
| 5,886,020 A | 3/1999 | Tang et al. | |
| 5,916,769 A | 6/1999 | Olsen et al. | |
| 5,952,374 A | 9/1999 | Clarkson | |
| 6,114,371 A | 9/2000 | Tang et al. | |
| 6,133,305 A | 10/2000 | Tang et al. | |
| 6,235,746 B1 | 5/2001 | Davis et al. | |
| 6,420,382 B2 | 7/2002 | Fraley et al. | |
| 6,498,165 B1 * | 12/2002 | Armstrong et al. | 514/275 |
| 6,498,176 B1 * | 12/2002 | Lackey et al. | 514/366 |
| 6,544,988 B1 * | 4/2003 | Bilodeau et al. | 514/233.2 |
| 6,762,180 B1 | 7/2004 | Roth et al. | |
| 6,958,335 B2 | 10/2005 | Buchdunger et al. | |
| 2002/0010203 A1 * | 1/2002 | Lipson et al. | 514/418 |
| 2002/0052386 A1 * | 5/2002 | Armistead et al. | 514/269 |
| 2003/0045451 A1 | 3/2003 | Bacus | |
| 2003/0091974 A1 | 5/2003 | Moussy et al. | |
| 2003/0176443 A1 | 9/2003 | Stein-Garlach et al. | |
| 2004/0028673 A1 | 2/2004 | Netzer et al. | |
| 2004/0241226 A1 | 12/2004 | Moussy et al. | |
| 2004/0242601 A1 | 12/2004 | Moussy et al. | |
| 2004/0242612 A1 | 12/2004 | Moussy et al. | |
| 2004/0259892 A1 | 12/2004 | Moussy et al. | |
| 2004/0259893 A1 | 12/2004 | Moussy et al. | |
| 2004/0266771 A1 | 12/2004 | Moussy et al. | |
| 2004/0266797 A1 | 12/2004 | Moussy et al. | |
| 2004/0266801 A1 | 12/2004 | Moussy et al. | |
| 2005/0054617 A1 | 3/2005 | Moussy et al. | |
| 2005/0059688 A1 | 3/2005 | Moussy et al. | |
| 2005/0089838 A1 | 4/2005 | Moussy et al. | |
| 2005/0176687 A1 | 8/2005 | Moussy et al. | |
| 2005/0222091 A1 | 10/2005 | Moussy et al. | |
| 2006/0166281 A1 | 7/2006 | Moussy et al. | |
| 2006/0204459 A1 | 9/2006 | Moussy et al. | |
| 2006/0275769 A1 | 12/2006 | Moses et al. | |

FOREIGN PATENT DOCUMENTS

| | | |
|---|---|---|
| DE | 198 24 922 A | 12/1999 |
| DE | 198 44 003 A | 3/2000 |
| EP | 0 403 238 A2 | 12/1990 |
| EP | 0 564 409 A | 10/1993 |
| EP | 0 586 020 A | 3/1994 |
| WO | WO 98 18782 | 5/1998 |
| WO | WO-9818782 * | 5/1998 |

(Continued)

OTHER PUBLICATIONS

UCSD School of Medicine News Apr. 29, 2002 pp. 1-2.*

(Continued)

*Primary Examiner*—Michael G Hartley
*Assistant Examiner*—Shirley V Gembeh
(74) *Attorney, Agent, or Firm*—Sughrue Mion, PLLC

(57) ABSTRACT

The present invention relates to a method for treating inflammatory bowel diseases (IBD), such as crohn's disease, comprising administering a tyrosine kinase inhibitor to a human in need of such treatment, more particularly a non-toxic, selective and potent c-kit inhibitor. Preferably, said inhibitor is unable to promote death of IL-3 dependent cells cultured in presence of IL-3.

4 Claims, No Drawings

FOREIGN PATENT DOCUMENTS

| | | |
|---|---|---|
| WO | WO 98 35056 A | 8/1998 |
| WO | WO 98 41525 A | 9/1998 |
| WO | WO 98 50356 A | 11/1998 |
| WO | WO 98 55152 A1 | 12/1998 |
| WO | WO 99 03854 A | 1/1999 |
| WO | WO 99 61028 A | 2/1999 |
| WO | WO 99 11643 A | 3/1999 |
| WO | WO 99 15500 A | 4/1999 |
| WO | WO 99 21859 A | 5/1999 |
| WO | WO 99 61422 A | 12/1999 |
| WO | WO 99 65908 A | 12/1999 |
| WO | WO 00 09098 A | 2/2000 |
| WO | WO 00 40971 A | 7/2000 |
| WO | WO 00 55139 A | 9/2000 |
| WO | WO 00 56709 A | 9/2000 |
| WO | WO 00 67794 A | 11/2000 |
| WO | WO 00 73297 A | 12/2000 |
| WO | WO 01 16130 A | 3/2001 |
| WO | WO 01 27081 A1 | 4/2001 |
| WO | WO 01 45689 A | 6/2001 |
| WO | WO 01 47517 A | 7/2001 |
| WO | WO 01 47950 A | 7/2001 |
| WO | WO 01 49287 A | 7/2001 |
| WO | 0164200 A2 | 9/2001 |
| WO | 0164674 A1 | 9/2001 |
| WO | WO 01 90104 A | 11/2001 |
| WO | WO 02 40486 A | 5/2002 |
| WO | WO 02 055517 A | 7/2002 |
| WO | WO 02 072578 A | 9/2002 |
| WO | 02080925 A1 | 10/2002 |
| WO | WO 03 002106 A3 | 1/2003 |
| WO | WO 03 035049 A2 | 5/2003 |
| WO | WO 03 035050 A2 | 5/2003 |
| WO | 03062215 A1 | 7/2003 |

OTHER PUBLICATIONS

Laboratory Assessment (1998) 2pages.*
Jahnsen et al., Scand. J. Gastroentterol. 2004 39 (2) Abstract only.*
Mielants et al., Baillieres Clin. Rhematol. 1996 10 (1) Abstract only).*
Topaly et al. (Leukemia 2001) 15, 342-347.*
Edelson et al. Pediatrics. 103(4), 766-771;1999 (Abstract Only).*
Gutknecht et al. Digestive Diseases and Sciences; 31(12), 1391 (1986).*
Mir Madjlessi et al. Digestive Diseases and Sciences; (1986) abstract only.*
Ma, Y. et al., "Indolinone Derivatives Inhibit Constitutively Activated Kit Mutants and Kill Neoplastic Mast Cells", *Journal of Investigative Dermatology*, NewYork, US, vol. 114, No. 2, Feb. 2000, pp. 392-394.
Imokawa, G. "Paracrine cytokine mechanisms of epidermal hyperpigmentation in UVB-melanosis, lentigo senilis and dematofibroma,", *Pigment Cell Research*, 2002, p. 34, vol. 15 Supp. 9.
James M. Grichnik, et al., "The SCF/KIT Pathway Plays a Critical Role in the Control of Normal Human Melanocyte Homeostasis," *The Journal of Investigative Dermatology*, vol. 111, No. 2, pp. 233-238, Aug. 1998, XP001133837.
Hachiya, A. et al., "The inhibitory effect of an extract of clove," *Journal of Investigative Dermatology*, Jul. 2002, p. 341, vol. 19, No. 1.
Hattori, H. et al., "The role of the epidermal stem cell factor (SCF)/c-kit cascade in the hyperpigmentation mechanism of lentigo senilis (LS)," *Pigment Cell Research*, 2002, p. 58, vol. 15, Supp. 9.
A. D. Laird et al, "SU6668 Is a Potent Antiangiogenic and Antitumor Agent that Induces Regression of Established Tumors", *Cancer Reseach*, vol. 60, pp. 4152-4160, 2000.
B. Smolich et al, "The antiangiogenic protein kinase inhibitors SU5416 and SU6668 inhibit the SCF receptor (c-kit) in a human myeloid leukemia cell line and in acute myeloid leukemia blasts", *Blood*, vol. 97, No. 5, pp. 1413-1421, 2001, XP002229742.
Sinha et al., "Implications for Src Kinases in Hematopoiesis: Signal Transduction Therapeutics", *Journal of Hematotherapy & Stem Cell Research*, vol. 8, pp. 465-480, 1999.
Sinha and Corey, *Signal Transduction Therapeutics*, pp. 471-480, 1999.
Asthma and Bone Health, *NIHORBD-NRC Fact Sheets*, 4 pages, Dec. 2005.
J. Lesinski, "Preventing Bone Loss", The Connection Newspapers, pp. 1-2, May 28, 2003.
www.hopkinsmedicine.org, Bone Loss from Chemotherapy, *Journal of Clinical Oncology*, vol. 19(14); pp. 3306-3311,2001.
Dolan et al., Rheumatology 41, www.rheumatology.oxfordjournals.org, pp. 1047-1051, 2002.
NIH Osteoporosis and Related Bone Diseases-National Resource Center, "What People With Inflammatory Bowel Disease Need to Know About Osteoporosis", pp. 1-4, updated Feb. 2005.
Krystal G W, et al., "Indolonone Tyrosine Kinase Inhibitors Block Kit Activation and Growth of Small Cell Lung Cancer Cells", vol. 61, No. 9, May 1, 2001, pp. 3660-3668.
Moosa, Mohammadi et al, "Structures of the Tyrosine Kinase Domain of Fibroblast Growth Factor Receptor in Complex with Inhibitors", *Science*, vol. 276, No. 5314, pp. 955-960, 1997.
Defazio, et al., "Interferon β-1a downregulates TNF α-induced intercellular adhesion molecule 1 expression on brain microvascular endothelial cells through a tyrosine kinase-dependent pathway", *Brain research*, vol. 881 (2): pp. 227-230, 2000.
J. Topaly, et al., Synergistic activity of the new ABL-specific tyrosine kinase inhibitor STI571 and chemotherapeutic drugs on BCR-ABL-positive chronic myelogenous leukemia cells, *Leukemia*, vol. 15, pp. 342-347,2001.
www.gsdl.com, "Laboratory Assessments: IBD and Allergies," GSDL Inflammatory Bowel Disease (IBD) and Allergies, 2 pages, Dec. 2005.
www.health.ucsd.edu, "Researchers Show Beneficial Role of Bacterial DNA in Fighting Inflammatory Bowel Disease," UCSD School of Medicine News Health Sciences Communications, 2 pages, Apr. 2002.
J. Jahnsen, et al., "Bone mineral density in patients with inflammatory bowel disease: a population-based prospective two-year follow-up study", Scand. J. Gastroenterol. Feb. 2004; 39(2), abstract only.
H. Mielants, et al., "Course of gut inflammation in spondylarthropathies and therapeutic consequences," Bailliers Clin. Rheumatol. Feb. 1996; 10(1): abstract only.
A. Yamataka, et al., Localization of Intestinal Pacemaker Cells and Synapses in the Muscle Layers of a Patient with Colonic Hypoganglionosis, *Journal of Pediatric Surgery*, vol. 31, No. 4, pp. 584-587, 1996.
A. Yamataka, et al., A Lack of Intestinal Pacemaker (c-kit) in Aganalionic Bowel of Patients with Hirschsprung's Disease, *Journal of Pediatric Surgery*, vol. 30, No. 3, pp. 441-444, 1995.
C. Njeh, et al, "Bone Loss: Quantitative imaging techniques for asses mass in rheumatoid arthritis", www.pubmedcentral, 9 pages, Dec. 2005.
R. Hicks, "Rheumatoid Arthritis", www.bbc.co.uk, 2 pages, Dec. 2005.
Healingwell.com, "Inflammatory Bowel Disease", www.healingwell.com, 11 pages, Dec. 2005.
Tada S, et al., "The significance of soluble IL-2 receptors in rheumatoid arthritis with interstitial pneumonia", *Aerugi*, vol. 41(3), pp. 428-33, 1992.
Adel A. EL-Gendy et al.: Synthesis and Antimicrobial Actibity of Some New 2-indolinone derived ozimes and spiro-isoxazolines.: *Archives of Pharmacal Research (SEOUL)*, vol. 23, No. 4, Aug. 2000, pp. 310-314, XP008014265; ISSN: 0253-6269.
A K S Gupta, et al.: "Synthesis of Some New Indolinone Derived hydrazones as Possible, Anti Bacterial Agents", *European Journal of Medicinal Chemistry*, vol. 18, No. 2, 1983, pp. 181-184, XP001109724; ISSN: 0223-5234.
S P Singh, et al.: "Indolinone Derivatives as Potential Antimicrobilal Agents" *Zentralblatt Fuer Mikrobiologie*, vol. 144, No. 2, 1989, pp. 105-109, XP008014264; ISSN: 0232-4393.
Marcus Maurer et al.: "The C-kit Ligand, Stem Cell Factor, can enhance innate immunity through effects on mast cells." *Journal of*

*Experimental Medicine*, vol. 188, No. 12, Dec. 21, 1998, pp. 2343-2348, XP008014256; ISSN 0022-1007.

Gary R. Klimpoel et al.: "A Role for Stem Cell Factor (SCF): C-kit Interaction(s) in the Intestinal Tract Response to Salmonell Typhimurium Infection.." *Journal of Experimental Medicine*, vol. 184, No. 1, 1996, pp. 271-276, XP008014258; ISSN: 0022-1007.

Andrea Koinig et al.: "Downregulation of C-kit Expression in Human Endotherlial Cells by Inflammatory Stimuli." *Blood*, vol. 90, No. 1, 1997, pp. 148-155, XP001148729, ISSN: 0006-4971.

Stephen J. Galli et al.: "Mast Cells as Sentinels of Innate Immunity." *Current Opinion in Immunology*, vol. 11, No. 1, Feb. 1999, pp. 53-59, XP004257657, ISSN: 0952-7915.

Medicine House, "Inflammatory Pain Syndromes Arthritis", www.medicinehouse.com, 13 pages, Jan. 2006.

D. Hollander, "Interstital Cystitis and Silk Allergy", *Med. Hypotheses*, vol. 43, pp. 155-156, 1994.

T. Maher et al., "Arthritis Rhinitis: Nothing to Sneeze At", Massachusetts College of Pharmacy and Health Sciences Continuing Education pp. 1-23, Jun. 2002.

D. Hele, "New approaches to modulation of inflammatory processes in airway disease models", *Respiratory research*, vol. 2, No. 5, 4 pages, 2001.

C. Oetzel, et al., The Tyrosine Kinase Inhibitor CGP 57148 (STI 571) Induces Apoptosis in BCR-ABL-positive Cells By Down-Regulating BCL-X, *Clin. Cancer Research*, vol. 6, pp. 1958-1968, 2000.

M. Carroll et al., "CGP 57148, a Tyrosine Kinase Inhibitor, Inhibits the Growth of Cells Expressing BCR-ABL, TEL-ABL, and TEL-PDGFR Fusion Proteins" *Blood*, vol. 90, No. 12, pp. 4947-4952, 1997.

P. Ferrao, Expression of Constitutively Activated Human c-Kit in Myb Transformed Early Myeloid Cells Leads to Factor Independence, Histiocytic Differentation, and Tumorigencity, *Blood*, vol. 90, No. 11, pp. 4569-4552, 1997.

M. Heinrich, "Inhibition of c-kit receptor tyrosine kinase activity by STI-571, a selective tyrosine kinase inhibitor", *Blood*, vol. 96, No. 3, pp. 925-932, 2000, XP001097629.

G. Bold, "New Anilinophthalazines as Potent and Orally Well Absorbed Inhibitors of the VEGF Receptor Tyrosine Kinases Useful as Antagonists of Tumor-Driven Angiogenesis", *J. Med. Chem*, vol. 43, pp. 2310-2323, 2000, XP000971347.

P. Traxler, "Protein tyrosine kinase inhibitors in cancer treatment", *Exp. Opin. Ther. Patents*, vol. 7, No. 6, pp. 571-585, XP002122590, 1997.

Srinivasan, Radhika, Interstital Cystitis Association, "Inflammatory Bowel Disease", www.ichelp.com, 2 pages, Jan. 2006.

R. Saban, "Mast cell regulation of inflammation and gene expression during antigen-induced bladder inflammation in mice", *Physiol Genomics*, vol. 7, pp. 35-43, 2001, XP001161208.

H. Nechustan, et al., Regulation of mast cell growth and proliferation, *Clin. Reviews in Oncology*, vol. 23, pp. 131-150, 1996, XP008019233.

J. Wood et al., "PTK787/ZK 222584, a Novel and Potent Inhibitor of Vascular Endothelial Growth Factor Receptor Tyrosine Kinases, Impairs Vascular Endothelial Growth Factor induced Responses and Tumor Growth after Oral Administration", *Cancer Research*, vol. 60, pp. 2178-2189, 2000, XP000971163.

Restriction Requirement issued, dated Sep. 7, 2006 in U.S. Appl. No. 10/482,037.

Response to Restriction Requirement filed Oct. 6, 2006 in U.S. Appl. No. 10/482,037.

Non-Final Office Action issued, dated Dec. 20, 2006 in U.S. Appl. No. 10/482,037.

Response to Non-Final OA filed Apr. 20, 2007 in U.S. Appl. No. 10/482,037.

Non-Final Office Action issued, dated Jan. 12, 2006 in U.S. Appl. No. 10/482,039.

Response to Non-Final Office Action filed Apr. 12, 2006 in U.S. Appl. No. 10/482,039.

Non-Final Office Action issued, dated Jul. 18, 2006 in U.S. Appl. No. 10/482,039.

Response to Non-Final Office Action filed Jan. 18, 2007 in U.S. Appl. No. 10/482,039.

Non-Final Office Action issued, dated Apr. 11, 2007 in U.S. Appl. No. 10/482,039.

Response to Non-Final Office Action filed Jul. 11, 2007 in U.S. Appl. No. 10/482,039.

Non-final Office Action issued, dated Jun. 4, 2007 in U.S. Appl. No. 10/490,334.

Restriction Requirement issued, dated Mar. 29, 2007 in U.S. Appl. No. 10/482,177.

Response to Restriction Requirement filed May 25, 2007 in U.S. Appl. No. 10/482,177.

Non-final Office Action issued, dated Aug. 17, 2007 in U.S. Appl. No. 10/482,177.

Non-final Office Action issued, dated Jan. 18, 2006 in U.S. Appl. No. 10/490,348.

Response to Non-final Office Action filed Apr. 18, 2006 in U.S. Appl. No. 10/490,348.

Non-final Office Action issued, dated Jul. 17, 2006 in U.S. Appl. No. 10/490,348.

Response to Non-final Office Action issued, dated Jan. 17, 2007 in U.S. Appl. No. 10/490,348.

Non-final Office Action issued, dated Aug. 22, 2007 in U.S. Appl. No. 10/490,348.

Restriction Requirement issued, dated Apr. 19, 2007 in U.S. Appl. No. 10/505,842.

Response to Restriction Requirement filed Aug. 17, 2007 in U.S. Appl. No. 10/505,842.

Non-final Office Action issued, dated Sep. 10, 2007 in U.S. Appl. No. 10/505,842.

Non-final Office Action issued, dated Jan. 20, 2006 in U.S. Appl. No. 10/482,035.

Response to Non-final Office Action filed Apr. 20, 2006 in U.S. Appl. No. 10/482,035.

Non-final Office Action issued, dated Nov. 2, 2006 in U.S. Appl. No. 10/482,035.

Response to Non-final Office Action filed Feb. 2, 2007 in U.S. Appl. No. 10/482,035.

Final Office Action issued, dated May 16, 2007 in U.S. Appl. No. 10/482,035.

S. P. Singh et al.: "Synthesis of some new 5 Bromo-3-Arylthiosemicarbazone-2-Indolinones as Antimicrobial Agents" *ACTA Pharmaceutica Jugoslavica*, vol. 36, No. 1, pp. 19-26, XP008014269; ISSN: 0001-6667 (1986).

S. Wilkinson et al, "Selective tyrosine kinase inhibitors", *Emerging Drugs*, vol. 5, No. 3, pp. 287-297, XP001062304 (2000).

Longley, B.J., et al., "New Approaches to Therapy for Mastocytosis a Case for Treatment with Kit Kinase Inhibitors", Hematology-Oncology Clinics of North America, W.B. Saunders, U.S,, vol. 14, No. 3, Jun. 2000, pp. 689-695.

International Search Report dated Feb. 16, 2004 for International Application No. PCT/IB03/01071.

Marya F. McCarty, et al., "Overexpression of PDGF-BB decreases colorectal and pancreatic cancer growth by increasing tumor pericyte content", The Journal of Clinical Investigation, 2007, 117(8): 2114-2122.

Final Office Action dated Nov. 29, 2007, in U.S. Appl. No. 10/482,033.

Final Office Action dated May 16, 2007, in U.S. Appl. No. 10/482,035.

Request for Continued Examination and 1.114 Amendment filed Nov. 16, 2007, in U.S. Appl. No. 10/482,035.

K.F. Chung, et al. British Medical Bulletin, 1992, 48:179-189 (Abstract only).

www.pueblo.gsa.gov/cic_text/health/atopic-dermatitis/defining.html, Jan. 22, 2000.

Notice of Non-Compliant Amendment dated Jul. 11, 2007, in U.S. Appl. No. 10/482,037.

Response to Notice of Non-Compliant Amendment filed Aug. 10, 2007, in U.S. Appl. No. 10/482,037.

Final Office Action dated Nov. 2, 2007, in U.S. Appl. No. 10/482,037.

Request for Continued Examination and 1.114 Amendment filed Mar. 3, 2008, in U.S. Appl. No. 10/482,037.

Final Office Action dated Oct. 3, 2007, in U.S. Appl. No. 10/482,039.

Request for Continued Examination and Response to Final Office Action filed Mar. 3, 2008, in U.S. Appl. No. 10/482,039.
1.111 Amendment filed Feb. 19, 2008, in U.S. Appl. No. 10/482,177.
Final Office Action dated May 29, 2008, in U.S. Appl. No. 10/482,177.
Wei Zhang et al., "Modulation of Tumor Angiogenesis by Stem Cell Factor", Cancer Research, 2000, 60: 6757-6762.
Restriction and Election of Species Requirements dated Oct. 15, 2007, in U.S. Appl. No. 10/482,758.
Response to Restriction and Election of Species Requirements filed Mar. 14, 2008, in U.S. Appl. No. 10/482,758.
Restriction Requirement issued, dated Oct. 2, 2007, in U.S. Appl. No. 10/490,287.
Response to Restriction Requirement filed Jan. 2, 2008, in U.S. Appl. No. 10/490,287.
Non-Final Office Action dated Mar. 18, 2008, in U.S. Appl. No. 10/490,287.
Frederic Feger et al., "The role of mast cells in host defense and their subversion by bacterial pathogens," Trends in Immunology, 2002, 23(3): 151-158.
Mosby's GenRx: The Complete Reference for Generic and Brand Drugs, 1998, pp. II-1991 to II-1994.
1.111 Amendment filed Dec. 4, 2007, in U.S. Appl. No. 10/490,334.
Non-Final Office Action dated Feb. 20, 2008, in U.S. Appl. No. 10/490,334.
1.111 Amendment filed May 20, 2008, in U.S. Appl. No. 10/490,334.
1.111 Amendment filed Dec. 21, 2007, in U.S. Appl. No. 10/490,348.
1.111 Amendment filed Dec. 10, 2007, in U.S. Appl. No. 10/505,842.
Final Office Action dated Mar. 13, 2008, in U.S. Appl. No. 10/505,842.
Non-Final Office Action dated Jun. 5, 2008, in U.S. Appl. No. 10/482,039.
Non-Final Office Action dated Jan. 30, 2008, in U.S. Appl. No. 10/482,035.
Non Final Office Action dated Jun. 17, 2008, in U.S. Appl. No. 10/482,758.
Patrick D. W. Kiely et al., "Mercuric Chloride-Induced Vasculitis in the Brown Norway Rat: αβ T Cell-Dependent and -Independent Phases", The Journal of Immunology, 1997, 159:5100-5106.
Non-Final Office Action dated Jun. 17, 2008, in U.S. Appl. No. 10/482,037.
Restriction and Election of Species Requirements dated Jun. 9, 2008, in U.S. Appl. No. 10/490,286.
Non-Final Office Action dated Jun. 25, 2008, in U.S. Appl. No. 10/490,348.
F. Aldenborg et al., "Proliferation and transepithelial migration of mucosal mast cells in interstitial cystitis", Immunology, 1986, 58:411-416.
M. Hohenfellner et al., "Interstitial cystitis: increased sympathetic innervation and related neuropeptide synthesis", J. Urol. 1992, 147(3):Abstract Only.
1.111 Response filed Jul. 30, 2008, in U.S. Appl. No. 10/482,035.
1.111 Amendment filed Aug. 18, 2008, in U.S. Appl. No. 10/490,287.
Non-Final Office Action dated Aug. 21, 2008, in U.S. Appl. No. 10/490,334.
Final Office Action dated Oct. 24, 2008, in U.S. Appl. No. 10/482,035.
David A. Walsh et al., "Angiogenesis in the pathogenesis of inflammatory joint and lung diseases", Arthritis Research, 2001, 3(3): 147-153.
Request for Continued Examination and 1.114 Amendment filed Dec. 1, 2008, in U.S. Appl. No. 10/482,177.
1.111 Amendment filed Sep. 25, 2008, in U.S. Appl. No. 10/490,348.
Notice of Appeal filed Dec. 5, 2008, in U.S. Appl. No. 10/482,039.
1.111 Amendment filed Dec. 17, 2008, in U.S. Appl. No. 10/482,758.
1.111 Amendment filed Dec. 17, 2008, in U.S. Appl. No. 10/482,037.
Final Office Action dated Jan. 22, 2009, in U.S. Appl. No. 10/490,287.
Dean D. Metcalfe et al., "Mast Cells", Physiological Reviews, 1997, 77(4): 1033-1079.
Final Office Action dated Jan. 12, 2009, in U.S. Appl. No. 10/490,348.

M.A. Golstein et al., "Chronic Interstitial Cystitis Occurring during the Shift between Rheumatoid Arthritis and Lupus", Clinical Rheumatology, 1994, 13(1): 119-122.
B. Foxwell et al., "Prospects for the development of small molecular weight compounds to replace anti-tumour necrosis factor biological agents", Ann Rheum Dis, 2003, 62 (Suppl. II): ii90-ii93.
Akira Inoue et al., "Suppression of surfactant protein A by an epidermal growth factor receptor tyrosine kinase inhibitor exacerbates lung inflammation", Cancer Sci., 2008, 99(8): 1679-1684.
Peter Traxler, "Tyrosine kinases as targets in cancer therapy-successes and failures", Expert Opin. Ther. Targets, 2003, 7(2): 215-234.
Fahad A. Al-Obeidi et al., "Development of inhibitors for protein tyrosine kinases", Oncogene, 2000, 19: 5690-5701.
1.116 Amendment filed Jan. 30, 2009 in U.S. Appl. No. 10/490,348.
Request for Continued Examination and 1.114 Response filed Feb. 5, 2009, in U.S. Appl. No. 10/482,039.
F. Dazzi et al., "Normal and Chronic phase CML hematopoietic cells repopulate NOD/SCID bone marrow with different kinetics and cell lineage representation", Hematol. J., 2000, 1(5):307-315.
Ariel Fernandez et al., "An anticancer C-Kit kinase inhibitor is reengineered to make it more active and less cardiotoxic", The Journal of Clinical Investigation, 2007, 117(12): 4044-4054.
C. Gelbmann et al., "Strictures in Crohn's disease are characterised by an accumulation of mast cells colocalised with laminin but not with fibronectin or vitronectin", Gut, 1999, 45(2):210-217.
Lee S. Rosen et al., "Phase I Experience with SU6668, a novel Multiple Receptor Tyrosine Kinase Inhibitor in Patients with Advanced Malignancies", Proc Am Soc Clin Oncol, 2001, 20 (Abstract 383).
Peter Vajkoczy et al., "Inhibition of Tumor Growth, Angiogenesis, and Microcirculation by the Novel Flk-Inhibitor SU5416 as Assessed by Intravital Multi-fluorescence Videomicroscopy", Neoplasia, 1999, 1(1): 31-41.
Request for Continued Examination and 1.114 Response filed Feb. 23, 2009, in U.S. Appl. No. 10/482,035.
Non-Final Office Action mailed Apr. 29, 2009 in U.S. Appl. No. 10/482,035.
Final Office Action mailed Mar. 30, 2009, in U.S. Appl. No. 10/482,037.
Request for Continued Examination and 1.114 Amendment filed Sep. 30, 2009 in U.S. Appl. No. 10/482,037.
Non-Final Office Action mailed Apr. 10, 2009 in U.S. Appl. No. 10/482,039.
Notice of Allowance mailed Aug. 26, 2009 in U.S. Appl. No. 10/482,039.
Non-Final Office Action dated Mar. 3, 2009, in U.S. Appl. No. 10/482,177.
Final Office Action mailed Mar. 4, 2009, in U.S. Appl. No. 10/482,758.
1.111 Amendment filed Dec. 22, 2008, in U.S. Appl. No. 10/490,334.
Non-Final Office Action mailed Apr. 28, 2009, in U.S. Appl. No. 10/490,334.
Non-Final Office Action mailed Mar. 19, 2009, in U.S. Appl. No. 10/490,348.
Restriction Requirement mailed Jan. 29, 2009, in U.S. Appl. No. 10/505,899.
Restriction Requirement mailed Jan. 19, 2007 in U.S. Appl. No. 10/523,018.
Restriction Requirement mailed Jan. 30, 2007 in U.S. Appl. No. 10/482,034.
Non-Final Office Action mailed Jan. 3, 2006 in U.S. Appl. No. 10/482,036.
1.111 Amendment filed Mar. 23, 2006 in U.S. Appl. No. 10/482,036.
Non-Final Office Action mailed Jul. 20, 2006 in U.S. Appl. No. 10/482,036.
Restriction Requirement mailed Oct. 21, 2005 in U.S. Appl. No. 10/482,040.
Restriction Requirement mailed Jan. 23, 2007 in U.S. Appl. No. 10/482,179.

* cited by examiner

USE OF TYROSINE KINASE INHIBITORS FOR TREATING INFLAMMATORY BOWEL DISEASES (IBD)

This application claims benefit to U.S. Provisional Application 60/301,405, filed Jun. 29, 2001.

The present invention relates to a method for treating inflammatory bowel diseases (IBD), such as crohn's disease, comprising administering a tyrosine kinase inhibitor to a human in need of such treatment, more particularly a non-toxic, selective and potent c-kit inhibitor. Preferably, said inhibitor is unable to promote death of IL-3 dependent cells cultured in presence of IL-3.

Inflammatory bowel disease is the term generally applied to four diseases of the bowel, namely Crohn's disease, ulcerative colitis, indeterminate colitis, and infectious colitis.

It is estimated that there may be up to 1,000,000 Americans with IBD. Males and females appear to be affected equally. While Crohn's disease afflicts people of all ages, it is primarily a disease of the young. Most cases are diagnosed before age 30, but the disease can occur in the sixth, seventh, and later decades.

Ulcerative colitis is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkuhn. A separation of the overlying mucosa from its blood supply leading to ulceration is observed. Signs and symptoms of the disease include cramping, lower abdominal pain, rectal bleeding, and frequent, loose discharges consisting mainly of blood, pus, and mucus with scanty fecal particles. A total colectomy may be required for acute severe or chronic ulcerative colitis.

Crohn's disease is also a chronic inflammatory disease of unknown etiology but, unlike ulcerative colitis, it can affect any part of the bowel. The most prominent feature of the disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. Most patients with Crohn's disease require surgery at some point, but subsequent relapse is common. Consequently, continuous medical treatment is necessary as of today.

Mucositis involves ulcerative breakdown of mucosal epithelial tissue, and is literally defined as inflammation of the mucous membrane. The physiopathology of mucositis involves a cascade of interactions among cells, cytokines and microflora. Early inflammatory phase is characterized by release of inflammatory cytokines in response to local tissue damage caused for example by cytotoxic agent(s);

The symptoms and signs of gastrointestinal mucositis include pain, bleeding, diarrhea, neovascularization, and progression to ulceration. Early signs of diarrhea include increased stool frequency, loose or watery stool, food aversion, increased bowel sounds, abdominal pain, and some loss of skin turgor indicative of dehydration. When the diarrhea is severe it may be associated with mucosal ulceration, bleeding, intestinal perforation and proctitis. Stool exam may reveal occult blood and fecal leukocytes.

Necrotizing enterocolitis is an inflammatory disease of unknown etiology that afflicts between 1-5% of all infants admitted to neonatal intensive care units, most of whom are premature infants. Signs and symptoms include abdominal distention, gastrointestinal hemorrhage, and feeding intolerance. The disease most often involves the ileum and colon, and is characterized by loss of epithelium and submucosal edema, ulcerations, and, in severe cases, transmural necrosis.

Today, the following groups of drugs are available for therapy of IBD:
- Aminosalicylates: aspirin-like drugs, which include sulfasalazine and mesalamine, given both orally and rectally.
- Corticosteroids: prednisone and methylprednisolone, available orally and rectally.
- Immune modifiers: azathioprine, 6MP, methotrexate.
- Antibiotics: metronidazole, ampicillin, ciprofloxacin, and others.

However, many of these anti-inflammatory compounds are ineffective in the treatment of IBD and can exacerbate experimental colitis in animals and activate quiescent inflammatory bowel disease in humans (Wallace et al., Gastroenterology, 102:18-27 (1992); Kaufmann et al., Annals of Internal Medicine, 107:513-516(1987)).

Because there are many mediators involved in IBD and since inflammation occurs in different areas having different mechanisms of action, it is difficult to predict what the correct therapy is for any specific inflammatory response. The use of histamine H.sub.3-receptor agonists for the treatment of IBD has been proposed in U.S. Pat. No. 6,028,095, but this treatment, while alleviating symptoms, does not respond to the causes of inflammatory bowel diseases.

Therefore, there is a need for alternative treatments of IBD that would provide a specific solution adapted to IBD.

More recently, IL-11 has been proposed for treating inflammatory bowel diseases (U.S. Pat. No. 6,126,933). IL-11 was discovered as a new cytokine stimulating the function of cells of the immune and hematopoietic systems (U.S. Pat. No. 5,854,028), such as macrophages (Burstein et al., Journal of Cellular Physiology (1992) 153:312; Bazan, Neuron (1991) 7:197; and Yang et al., BioFactors (1992) 4:15-21).

The invention goes to the opposite direction since it has been found that the causes of inflammation in IBD in directly or indirectly due to the presence of numerous mast cells in the bowel, leading to the activation of the immune system mediated inflammatory response.

Mast cells (MC) are tissue elements derived from a particular subset of hematopoietic stem cells that express CD34, c-kit and CD13 antigens (Kirshenbaum et al, Blood, 94: 2333-2342, 1999 and Ishizaka et al, Curr Opin Immunol. 5: 937-43, 1993). Immature MC progenitors circulate in the bloodstream and differentiate in tissues. These differentiation and proliferation processes are under the influence of cytokines, one of utmost importance being Stem Cell Factor (SCF), also termed Kit ligand (KL), Steel factor (SL) or Mast Cell Growth Factor (MCGF). SCF receptor is encoded by the protooncogene c-kit, that belongs to type III receptor tyrosine kinase subfamily (Boissan and Arock, J Leukoc Biol. 67: 135-48, 2000). This receptor is also expressed on others hematopoietic or non hematopoietic cells. Ligation of c-kit receptor by SCF induces its dimerization followed by its transphosphorylation, leading to the recruitement and activation of various intracytoplasmic substrates. These activated substrates induce multiple intracellular signaling pathways responsible for cell proliferation and activation (Boissan and Arock, 2000). Mast cells are characterized by their heterogeneity, not only regarding tissue location and structure but also at the functional and histochemical levels (Aldenborg and Enerback., Histochem. J. 26: 587-96, 1994; Bradding et al. J Immunol. 155: 297-307, 1995; Irani et al, J Immunol. 147: 247-53, 1991; Miller et al, Curr Opin Immunol. 1: 637-42, 1989 and Welle et al, J Leukoc Biol. 61: 233-45, 1997).

Several inflammatory disorders of the intestine are characterised by enhanced expression of tumour necrosis factor alpha (TNF-alpha). Monocytes and macrophages have been suggested as a major cellular source of TNF-alpha in human gut, whereas mast cells, although known to be capable of producing TNF-alpha, have been poorly examined in this respect. One of the first cytokines found to be produced by mast cells was TNF-a which was detected primarily in rodent mast cells and mast cell lines (Gordon et al. (1991), J Exp Med 174: 103-107). In animal models, mast cells derived TNF-a was found to be responsible for the regulation of bacterial infection, and for the influx of neutrophils observed during immune complex peritonitis and IgE dependent cutaneous or gastric inflammation (Furuta et al. (1997) Gastroenterology 113: 1560-1569; Zhang et al. (1992), Science 258: 1957-1959; Wershil et al. (1991) J Clin Invest 87: 446-453 and Bischoff et al. (1999). Gut 44: 643-652. It was shown that mast cells are an important source of TNF-a in the human intestinal mucosa. Moreover, they also demonstrated that % of TNF-a positive cells and the % of tryptase positive TNF producing cells were higher in inflamed tissue (in Crohn's disease) compared with macroscopically normal tissue. Former electron microscopic studies performed in patients with Crohn's disease revealed that number of mast cells was markedly increased and were found predominantly in edematous submucosa and between smooth muscle in the muscular coats of the involved gut (Dvorak et al. (1980). Hum Pathol 11(6): 606-619).

In connection with the invention, evidence of focal and complete degranlulation of mast cells was frequently observed. Besides, mast cells produce a large variety of mediators categorized here into three groups: preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-a, GM-CSF, MIP-1a, MIP-1b and IFN-g). Then, liberation by activated mast cells of mediators (TNF-a, histamine, leucotrienes, prostaglandines etc. . . . ) is proposed here to induce acute or chronic inflammation as it can be observed in Crohn's disease.

So, a new route for treating inflammatory bowel diseases, such as crohn's disease, is provided, which consists of destroying mast cells playing a role in IBD pathogenesis. It has been found that tyrosine kinase inhibitors and more particularly c-kit inhibitors are especially suited for treating these diseases.

DESCRIPTION

The present invention relates to a method for treating inflammatory bowel diseases (IBD) comprising administering a tyrosine kinase inhibitor to a human in need of such treatment.

Tyrosine kinase inhibitors are selected for example from bis monocyclic, bicyclic or heterocyclic aryl compounds (WO 92/20642), vinylene-azaindole derivative (WO 94/14808) and 1-cycloproppyl-4-pyridyl-quinolones (U.S. Pat. No. 5,330,992), Styryl compounds (U.S. Pat. No. 5,217,999), styryl-substituted pyridyl compounds (U.S. Pat. No. 5,302,606), seleoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrol-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

Preferably, said tyrosine kinase inhibitors are unable to promote death of IL-3 dependent cells cultured in presence of IL-3.

In another embodiment, the invention is directed to a method for treating inflammatory bowel diseases comprising administering a c-kit inhibitor to a human in need of such treatment.

Preferably, said c-kit inhibitor is a non-toxic, selective and potent c-kit inhibitor. Such inhibitors can be selected from the group consisting of indolinones, pyrimidine derivatives, pyrrolopyrimidine derivatives, quinazoline derivatives, quinoxaline derivatives, pyrazoles derivatives, bis monocyclic, bicyclic or heterocyclic aryl compounds, vinylene-azaindole derivatives and pyridyl-quinolones derivatives, styryl compounds, styryl-substituted pyridyl compounds, seleoindoles, selenides, tricyclic polyhydroxylic compounds and benzylphosphonic acid compounds.

Among preferred compounds, it is of interest to focus on pyrimidine derivatives such as N-phenyl-2-pyrimidine-amine derivatives (U.S. Pat. No. 5,521,184 and WO 99/03854), indolinone derivatives and pyrrol-substituted indolinones (U.S. Pat. No. 5,792,783, EP 934 931, U.S. Pat. No. 5,834,504), U.S. Pat. No. 5,883,116, U.S. Pat. No. 5,883, 113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940), 4-amino-substituted quinazolines (U.S. Pat. No. 3,470,182), 4-thienyl-2-(1H)-quinazolones, 6,7-dialkoxyquinazolines (U.S. Pat. No. 3,800,039), aryl and heteroaryl quinazoline (U.S. Pat. No. 5,721,237, U.S. Pat. No. 5,714,493, U.S. Pat. No. 5,710,158 and WO 95/15758), 4-anilinoquinazoline compounds (U.S. Pat. No. 4,464,375), and 4-thienyl-2-(1H)-quinazolones (U.S. Pat. No. 3,551,427).

So, preferably, the invention relates to a method for treating inflammatory bowel diseases comprising administering to a human in need of such treatment a non toxic, potent and selective c-kit inhibitor.

Such inhibitor can be selected from pyrimidine derivatives, more particularly N-phenyl-2-pyrimidine-amine derivatives of formula I:

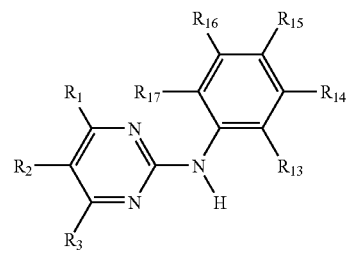

wherein the R1, R2, R3, R13 to R17 groups have the meaning depicted in EP 564 409 B1, incorporated herein in the description.

Preferably, the N-phenyl-2-pyrimidine-amine derivative is selected from the compounds corresponding to formula II:

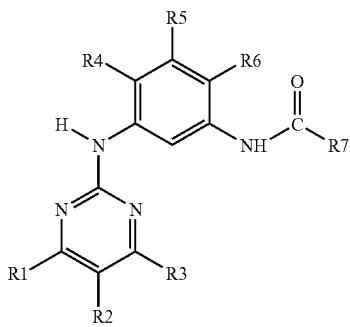

Wherein R1, R2 and R3 are independently chosen from H, F, Cl, Br, I, a C1-C5 alkyl or a cyclic or heterocyclic group, especially a pyridyl group;

R4, R5 and R6 are independently chosen from H, F, Cl, Br, I, a C1-C5 alkyl, especially a methyl group;

and R7 is a phenyl group bearing at least one substituent, which in turn possesses at least one basic site such as an amino function.

Preferably, R7 is the following group:

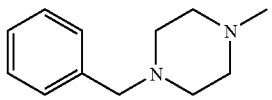

Among these compounds, the preferred are defined as follows:

R1 is a heterocyclic group, especially a pyridyl group,

R2 and R3 are H,

R4 is a C1-C3 alkyl, especially a methyl group,

R5 and R6 are H, and R7 is a phenyl group bearing at least one substituent, which in turn possesses at least one basic site, such as an amino function, for example the group:

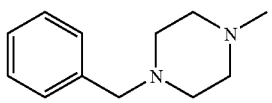

Therefore, in a preferred embodiment, the invention relates to a method for treating IBD, more particularly crohn's disease, comprising the administration of an effective amount of the compound known in the art as CGP57148B:

4-(4-méthylpipérazine-1-ylméthyl)-N-(4-méthyl-3-(4-pyridine-3-yl)pyrimidine-2 ylamino)phényl]-benzamide corresponding to the following formula:

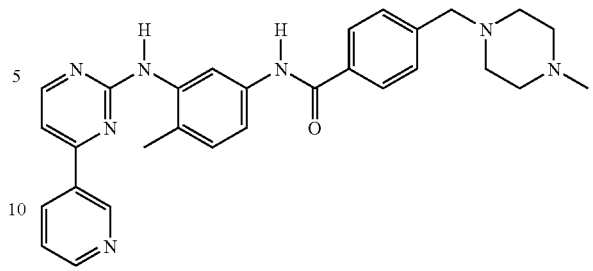

The preparation of this compound is described in example 21 of EP 564 409 and the β-form, which is particularly useful is described in WO 99/03854.

Alternatively, the c-kit inhibitor can be selected from:
 indolinone derivatives, more particularly pyrrol-substituted indolinones,
 monocyclic, bicyclic aryl and heteroaryl compounds, quinazoline derivatives,
  and quinaxolines, such as 2-phényl-quinaxoline derivatives, for example 2-phenyl-6,7-dimethoxy quinaxoline.

In a preferred aspect, the invention contemplated the method mentioned above, wherein said c-kit inhibitor is unable to promote death of IL-3 dependent cells cultured in presence of IL-3.

In a further embodiment, c-kit inhibitors as mentioned above are inhibitors of activated c-kit. In frame with the invention, the expression "activated c-kit" means a constitutively activated-mutant c-kit including at least one mutation selected from point mutations, deletions, insertions, but also modifications and alterations of the natural c-kit sequence (SEQ ID No1). Such mutations, deletions, insertions, modifications and alterations can occur in the transphosphorylase domain, in the juxtamembrane domain as well as in any domain directly or indirectly responsible for c-kit activity. The expression "activated c-kit" also means herein SCF-activated c-kit. Preferred and optimal SCF concentrations for activating c-kit are comprised between $5.10^{-7}$ M and $5.10^{-6}$ M, preferably around $2.10^{-6}$ M. In a preferred embodiment, the activated-mutant c-kit in step a) has at least one mutation proximal to Y823, more particularly between amino acids 800 to 850 of SEQ ID No1 involved in c-kit autophosphorylation, notably the D816V, D816Y, D816F and D820G mutants. In another preferred embodiment, the activated-mutant c-kit in step a) has a deletion in the juxtamembrane domain of c-kit. Such a deletion is for example between codon 573 and 579 called c-kit d(573-579). The point mutation V559G proximal to the juxtamembrane domain c-kit is also of interest.

In this regard, the invention contemplates a method for treating inflammatory bowel diseases comprising administering to a human in need of such treatment a compound that is a selective, potent and non toxic inhibitor of activated c-kit obtainable by a screening method which comprises:

a) bringing into contact (i) activated c-kit and (ii) at least one compound to be tested; under conditions allowing the components (i) and (ii) to form a complex, b) selecting compounds that inhibit activated c-kit, c) testing and selecting a subset of compounds identified in step b), which are unable to promote death of IL-3 dependent cells cultured in presence of IL-3.

This screening method can further comprise the step consisting of testing and selecting a subset of compounds identified in step b) that are inhibitors of mutant activated c-kit (for example in the transphosphorylase domain), which are also capable of inhibiting SCF-activated c-kit wild.

Alternatively, in step a) activated c-kit is SCF-activated c-kit wild.

A best mode for practicing this method consists of testing putative inhibitors at a concentration above 10 µM in step a). Relevant concentrations are for example 10, 15, 20, 25, 30, 35 or 40 µM.

In step c), IL-3 is preferably present in the culture media of IL-3 dependent cells at a concentration comprised between 0.5 and 10 ng/ml, preferably between 1 to 5 ng/ml.

Examples of IL-3 dependent cells include but are not limited to:

cell lines naturally expressing and depending on c-kit for growth and survival. Among such cells, human mast cell lines can be established using the following procedures: normal human mast cells can be infected by retroviral vectors containing sequences coding for a mutant c-kit comprising the c-kit signal peptide and a TAG sequence allowing to differentiate mutant c-kits from c-kit wild expressed in hematopoetic cells by means of antibodies.

This technique is advantageous because it does not induce cellular mortality and the genetic transfer is stable and gives satisfactory yields (around 20%). Pure normal human mast cells can be routinely obtained by culturing precursor cells originating from blood obtained from human umbilical vein. In this regard, heparinated blood from umbilical vein is centrifuged on a Ficoll gradient so as to isolate mononucleated cells from other blood components. CD34+ precursor cells are then purified from the isolated cells mentioned above using the immunomagnetic selection system MACS (Miltenyi biotech). CD34+ cells are then cultured at 37° C. in 5% $CO_2$ atmosphere at a concentration of $10^5$ cells per ml in the medium MCCM (α-MEM supplemented with L-glutamine, penicillin, streptomycin, 5, $10^{-5}$ M β-mercaptoethanol, 20% veal fœtal serum, 1% bovine albumin serum and 100 ng/ml recombinant human SCF. The medium is changed every 5 to 7 days. The percentage of mast cells present in the culture is assessed each week, using May-Grünwal Giemsa or Toluidine blue coloration. Anti-tryptase antibodies can also be used to detect mast cells in culture. After 10 weeks of culture, a pure cellular population of mast cells (<98%) is obtained.

It is possible using standard procedures to prepare vectors expressing c-kit for transfecting the cell lines established as mentioned above. The cDNA of human c-kit has been described in Yarden et al., (1987) EMBO J. 6 (11), 3341-3351. The coding part of c-kit (3000 bp) can be amplified by PCR and cloned, using the following oligonucleotides:

```
5'AAGAAGAGATGGTACCTCGAGGGGTGACCC3'    (SEQ ID No2)
sens

5'CTGCTTCGCGGCCGCGTTAACTCTTCTCAACCA3' (SEQ ID No3)
antisens
```

The PCR products, digested with NotI and XhoI, has been inserted using T4 ligase in the pFlag-CMV vector (SIGMA), which vector is digested with NotI and XhoI and dephosphorylated using CIP (Biolabs). The pFlag-CMV-c-kit is used to transform bacterial clone XL1-blue. The transformation of clones is verified using the following primers:

```
5'AGCTCGTTTAGTGAACCGTC3'    (SEQ ID No4)  sens,

5'GTCAGACAAAATGATGCAAC3'    (SEQ ID No5)  antisens.
```

Directed mutagenesis is performed using relevant cassettes is performed with routine and common procedure known in the art.

The vector Migr-1 (ABC) can be used as a basis for constructing retroviral vectors used for transfecting mature mast cells. This vector is advantageous because it contains the sequence coding for GFP at the 3' and of an IRES. These features allow to select cells infected by the retrovirus using direct analysis with a fluorocytometer. As mentioned above, the N-terminal sequence of c-kit c-DNA can be modified so as to introduce a Flag sequence that will be useful to discriminating heterogeneous from endogenous c-kit.

Other IL-3 dependent cell lines that can be used include but are not limited to:

BaF3 mouse cells expressing wild-type or mutated form of c-kit (in the juxtamembrane and in the catalytic sites) are described in Kitayama et al, (1996), Blood 88, 995-1004 and Tsujimura et al, (1999), Blood 93, 1319-1329.

IC-2 mouse cells expressing either c-kit$^{WT}$ or c-kit$^{D814Y}$ are presented in Piao et al, (1996), Proc. Natl. Acad. Sci. USA 93, 14665-14669.

IL-3 independent cell lines are:

HMC-1, a factor-independent cell line derived from a patient with mast cell leukemia, expresses a juxtamembrane mutant c-kit polypeptide that has constitutive kinase activity (Furitsu T et al, J Clin Invest. 1993; 92:1736-1744; Butterfield et al, Establishment of an immature mast cell line from a patient with mast cell leukemia. Leuk Res. 1988; 12:345-355 and Nagata et al, Proc Natl Acad Sci U S A. 1995; 92:10560-10564).

P815 cell line (mastocytoma naturally expressing c-kit mutation at the 814 position) has been described in Tsujimura et al, (1994), Blood 83, 2619-2626.

The extent to which component (ii) inhibits activated c-kit can be measured in vitro or in vivo. In case it is measured in vivo, cell lines expressing an activated-mutant c-kit, which has at least one mutation proximal to Y823, more particularly between amino acids 800 to 850 of SEQ ID No1 involved in c-kit autophosphorylation, notably the D816V, D816Y, D816F and D820G mutants, are preferred.

Example of cell lines expressing an activated-mutant c-kit are as mentioned.

In another preferred embodiment, the method further comprises the step consisting of testing and selecting compounds capable of inhibiting c-kit wild at concentration below 1 µm. This can be measured in vitro or in vivo.

Therefore, compounds are identified and selected according to the method described above are potent, selective and non-toxic c-kit wild inhibitors.

Alternatively, the screening method as defined above can be practiced in vitro. In this regard, the inhibition of mutant-activated c-kit and/or c-kit wild can be measured using standard biochemical techniques such as immunoprecipitation and western blot. Preferably, the amount of c-kit phosphorylation is measured.

In a still further embodiment, the invention contemplates a method for treating inflammatory bowel diseases as depicted above wherein the screening comprises:

a) performing a cellular assay with cells selected from cells expressing a mutant c-kit (for example in the transphosphorylase domain), which mutant is a permanent activated c-kit, with a plurality of test compounds to identify a subset of candidate compounds targeting activated c-kit, each having all IC50<10 µM, by measuring the extent of cell death, b) performing a cellular assay with cells expressing c-kit wild said subset of candidate compounds identified in step (a), said cells being IL-3 dependent cells cultured in presence of IL-3, to identify a subset of candidate compounds targeting specifically c-kit, c) performing a cellular assay with cells selected from cells expressing c-kit, with the subset of compounds identified in step b) and selecting a subset of candidate compounds targeting c-kit wild, each having an IC50<10 µM, preferably an IC50<1 µM, by measuring the extent of cell death.

Here, the extent of cell death can be measured by 3H thymidine incorporation, the trypan blue exclusion method or flow cytometry with propidium iodide. These are common techniques routinely practiced in the art.

The method according to the invention includes preventing, delaying the onset and/or treating IBD.

More particularly, the invention contemplates the method defined above for treating Crohn's disease, mucositis, ulcerative colitis, and necrotizing enterocolitis.

Therefore, the invention embraces the use of the compounds defined above to manufacture a medicament for treating IBD, such as Crohn's disease, mucositis, ulcerative colitis, and necrotizing enterocolitis.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising, excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Controlled as well as prolonged release formulation are contemplated.

Pharmaceutical preparations for oral use can be obtained through combination of active compounds with solid excipient. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

The pharmaceutical composition may be provided as a salt and can be formed with many acids including but not limited to, hydrochloric, sulfuric, acetic, lactic, tartaric, malic, and succine, acids, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions suitable for use in the invention include compositions wherein c-kit inhibitors are contained in an effective amount to achieve the intended purpose. The determination of an effective dose is well within the capability of those skilled in the art. A therapeutically effective dose refers to that amount of active ingredient, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therpeutic effects is the therapeutic index, and it can be expressed as the ratio, LD50/ED50. Pharmaceutical compositions which exhibit large therapeutic indices are preferred. As mentioned above, a tyrosine kinase inhibitor and more particularly a c-kit inhibitor according to the invention is unable to promote death of IL-3 dependent cells cultured in presence of IL-3.

The invention claimed is:

1. A method for treating inflammatory bowel diseases (IBD) comprising administering an effective amount of the following compound

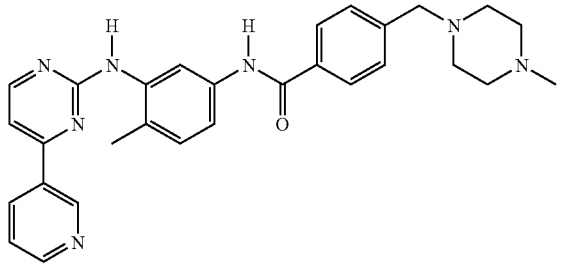

4-(4-methylpiperazine-1-ylmethyl)-N-[4-methyl-3-[(4-pyridine-3-ylpyrimidine-2-yl)amino]phenyl]-benzamide, or a pharmaceutically acceptable salt thereof, to a human in need of such treatment.

2. The method according to claim 1 wherein the inflammatory bowel disease is Crohn's disease.

3. The method according to claim 1, wherein the inflammatory bowel disease is ulcerative colitis.

4. The method according to claim 1, wherein the inflammatory bowel disease is necrotizing enterocolitis.

* * * * *

SEQUENCE LISTING

<160> NUMBER OF SEQ ID NOS: 5

<210> SEQ ID NO 1
<211> LENGTH: 976
<212> TYPE: PRT
<213> ORGANISM: Homo sapiens
<220> FEATURE:
<223> OTHER INFORMATION: Human c-kit

<400> SEQUENCE: 1

Met Arg Gly Ala Arg Gly Ala Trp Asp Phe Leu Cys Val Leu Leu Leu
 1               5                  10                  15

Leu Leu Arg Val Gln Thr Gly Ser Ser Gln Pro Ser Val Ser Pro Gly
             20                  25                  30

Glu Pro Ser Pro Pro Ser Ile His Pro Gly Lys Ser Asp Leu Ile Val
         35                  40                  45

Arg Val Gly Asp Glu Ile Arg Leu Leu Cys Thr Asp Pro Gly Phe Val
     50                  55                  60

Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                 85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

-continued

```
Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765
```

```
Leu Leu Ser Phe Ser Tyr Gln Val Ala Lys Gly Met Ala Phe Leu Ala
    770             775                 780
Ser Lys Asn Cys Ile His Arg Asp Leu Ala Ala Arg Asn Ile Leu Leu
785             790                 795                 800
Thr His Gly Arg Ile Thr Lys Ile Cys Asp Phe Gly Leu Ala Arg Asp
            805                 810                 815
Ile Lys Asn Asp Ser Asn Tyr Val Val Lys Gly Asn Ala Arg Leu Pro
            820                 825                 830
Val Lys Trp Met Ala Pro Glu Ser Ile Phe Asn Cys Val Tyr Thr Phe
            835                 840                 845
Glu Ser Asp Val Trp Ser Tyr Gly Ile Phe Leu Trp Glu Leu Phe Ser
    850                 855                 860
Leu Gly Ser Ser Pro Tyr Pro Gly Met Pro Val Asp Ser Lys Phe Tyr
865                 870                 875                 880
Lys Met Ile Lys Glu Gly Phe Arg Met Leu Ser Pro Glu His Ala Pro
                885                 890                 895
Ala Glu Met Tyr Asp Ile Met Lys Thr Cys Trp Asp Ala Asp Pro Leu
            900                 905                 910
Lys Arg Pro Thr Phe Lys Gln Ile Val Gln Leu Ile Glu Lys Gln Ile
            915                 920                 925
Ser Glu Ser Thr Asn His Ile Tyr Ser Asn Leu Ala Asn Cys Ser Pro
    930                 935                 940
Asn Arg Gln Lys Pro Val Val Asp His Ser Val Arg Ile Asn Ser Val
945                 950                 955                 960
Gly Ser Thr Ala Ser Ser Ser Gln Pro Leu Leu Val His Asp Asp Val
                965                 970                 975

<210> SEQ ID NO 2
<211> LENGTH: 30
<212> TYPE: DNA
<213> ORGANISM: Homo sapiens
<220> FEATURE:
<223> OTHER INFORMATION: Primer

<400> SEQUENCE: 2
aagaagagat ggtacctcga ggggtgaccc                                      30

<210> SEQ ID NO 3
<211> LENGTH: 33
<212> TYPE: DNA
<213> ORGANISM: Homo sapiens
<220> FEATURE:
<223> OTHER INFORMATION: Primer

<400> SEQUENCE: 3
ctgcttcgcg gccgcgttaa ctcttctcaa cca                                  33

<210> SEQ ID NO 4
<211> LENGTH: 20
<212> TYPE: DNA
<213> ORGANISM: Homo sapiens
<220> FEATURE:
<223> OTHER INFORMATION: Primer

<400> SEQUENCE: 4
agctcgttta gtgaaccgtc                                                 20

<210> SEQ ID NO 5
<211> LENGTH: 20
<212> TYPE: DNA
```

```
<213> ORGANISM: Homo sapiens
<220> FEATURE:
<223> OTHER INFORMATION: Primer

<400> SEQUENCE: 5
gtcagacaaa atgatgcaac                                             20
```